July 14, 1953 H. M. TIRET Plant Pat. 1,203
FUCHSIA PLANT
Filed Feb. 27, 1952
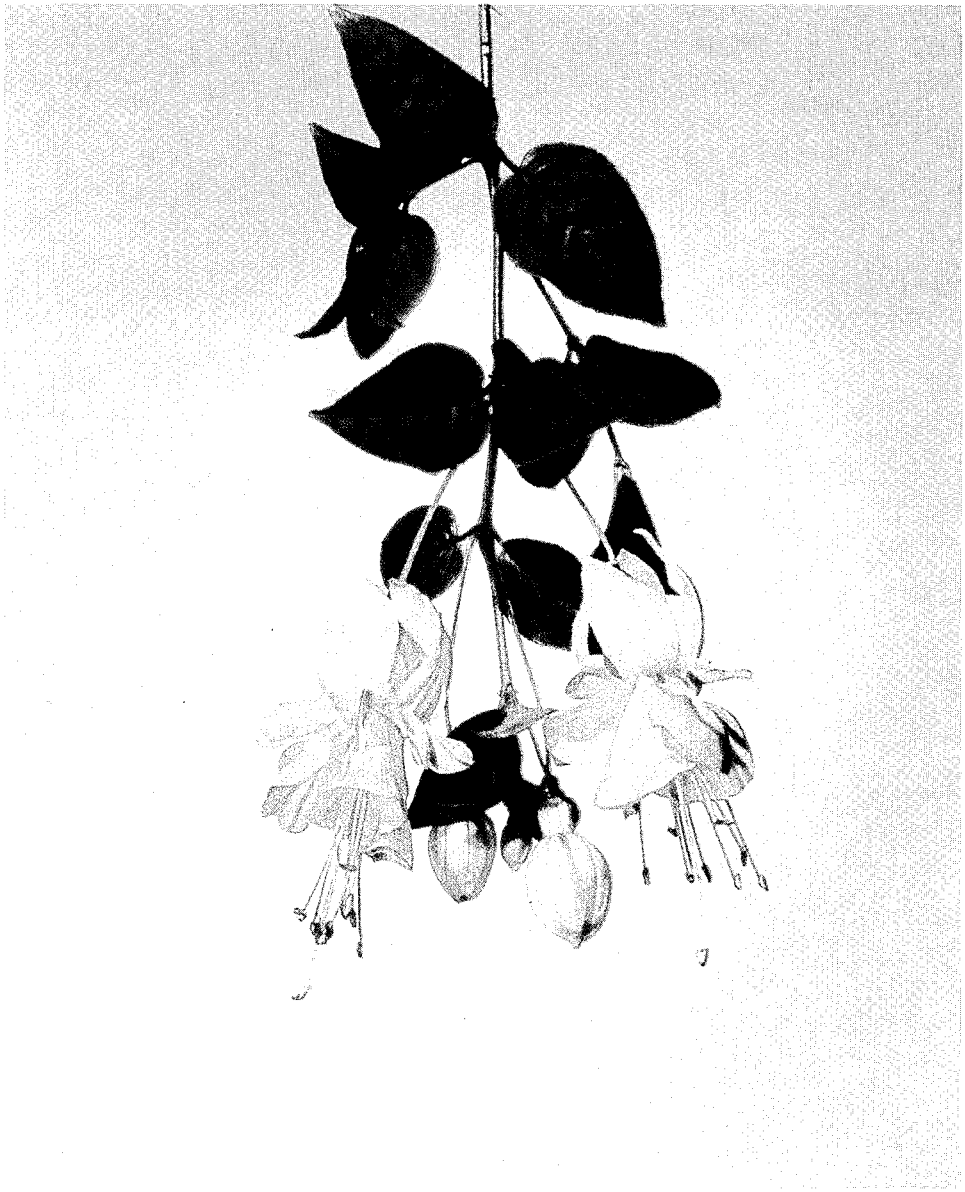
Inventor
Horace M. Tiret Patented July 14, 1953

Plant Pat. 1,203

UNITED STATES PATENT OFFICE 1,203

FUCHSIA PLANT

Horace M. Tiret, San Francisco, Calif.

Application February 27, 1952, Serial No. 273,706

1 Claim. (Cl. 47—60)

This invention relates to a new and improved fuchsia plant, the principal new and different characteristic of which is the combination of the broad, recurved pale crimson sepals with the pale orchid purple petals.

The plant was derived as a hybrid from Treasure (unpatented), a fuchsia introduced by the late Gustav Niederholzer, and applicant's seedling (unpatented) and not introduced to the trade, namely 3/36/5, the figures representing applicant's own breeding symbols. The fuchsia plant is distinguished principally by its deeply creased dark green foliage, vigorous bushy habit of growth, distinctive pale orchid purple coloring of the petals and the recurved pale crimson sepals, which has not previously been found in this combination in any fuchsia plant, and has been asexually reproduced at Palo Alto, Santa Clara County, California, by cuttings which retained the characteristics of the parent fuchsia.

The plant is a bushy upright variety, and grows vigorously, throwing numerous vertical and parallel branches during the process of growth. When the plant blooms, the short and broad buds, colored green at the tips, and shading to white and pale crimson at the base, open into large, double open flowers. The flower is pale orchid purple (Horticultural Color Chart 31/3). The flower has no fragrance.

In the accompanying drawing, the figure shows a typical branch tip, including both a bud and fully opened blossom, the drawing representing approximately actual size.

A detailed description of this new variety of fuchsia plant follows:

*Habit of growth.*—Strong, bushy, upright variety, and grows vigorously, throwing out numerous vertical and parallel branches from the roots, and whose branches are in turn self-branching. Flowers occur both along the stem and at the tips of the branches.

*Foliage.*—Medium sized, dark green leaves, deeply veined, having serrated edges and evenly spaced along the branches. The leaves are of a general broad heart shape. The buds are short and full and have a color of green at the tips, shading to white and pale crimson at the base.

*Flower.*—The flower is double, of large size for the genus. The corolla is open and flaring. The flower is fairly resistant to wilting at high atmospheric temperature, and grows equally well in the cooler climate of the west. The color is pale orchid purple (Horticultural Color Chart 31/3) which is the outstanding, different and distinctive feature of this plant. There are, in addition to the center petals, many short surrounding outer petals, the color of which is pastel petunia purple (Horticultural Color Chart 32/2).

*Ovary.*—Medium small and light green.

*Tube.*—Short, broad and flesh colored.

*Petals.*—From twelve to eighteen petals occur to each flower, and the outer petals form a flaring skirt for those in the center. The outer petals are pastel petunia purple, and those in the center are pale orchid purple, all as above described.

*Stamens.*—The stamens are long, approximately 1⅝ inches in length measured from the seed pod, and of a maroon color, and terminate short of the long pistil, approximately 2⅞ inches in length, measured from the seed pod, having a yellow tip which hangs below the cluster of stamens.

*Sepals.*—The sepals are short, with the underside broad and recurved, having a crepe-like texture. The under color is pale crimson (Horticultural Chart 22/3). The upper surface is smooth and colored white with green tips shading to pale crimson at the base.

*Parentage.*—Treasure (unpatented) by the late Gustav Niederholzer, and applicant's seedling (unpatented) 3/36/5, the figures representing applicant's own breeding symbols.

It is noted that the foliage and flowers will vary somewhat with the seasons and growing conditions; however, the fuchsia plant is clearly differentiated from others by the pale orchid purple color of the petals.

Having thus disclosed my discovery I claim:

The new and distinct variety of fuchsia plant herein described and illustrated, characterized by the broad, recurved pale crimson sepals in combination with the pale orchid petals.

HORACE M. TIRET.

References Cited in the file of this patent

UNITED STATES PATENTS

| Number | Name | Date |
|---|---|---|
| Pl. Pt. 1,110 | Waltz | July 1, 1952 |